US008696670B2

(12) United States Patent
Chico Roca

(10) Patent No.: US 8,696,670 B2
(45) Date of Patent: Apr. 15, 2014

(54) FIXATION DEVICE FOR THE FIXATION OF BONE FRAGMENTS

(71) Applicant: Neos Surgery, S.L., Cerdanyola Del Valles (ES)

(72) Inventor: Lluis Chico Roca, Badalona (ES)

(73) Assignee: Neos Surgery, S.L., Cerdanyola del Valles (ES)

( * ) Notice: Subject to any disclaimer, the term of this patent is extended or adjusted under 35 U.S.C. 154(b) by 0 days.

(21) Appl. No.: 13/705,146

(22) Filed: Dec. 4, 2012

(65) Prior Publication Data

US 2013/0165978 A1 Jun. 27, 2013

Related U.S. Application Data

(63) Continuation of application No. 12/671,165, filed as application No. PCT/EP2008/060279 on Aug. 5, 2008, now Pat. No. 8,403,930.

(30) Foreign Application Priority Data

Aug. 10, 2007 (ES) .................................. 200702258

(51) Int. Cl.
*A61B 17/56* (2006.01)
*A61B 17/58* (2006.01)
*A61B 17/82* (2006.01)
*A61F 2/30* (2006.01)

(52) U.S. Cl.
USPC ................. 606/74; 606/324; 606/70; 606/71

(58) Field of Classification Search
USPC ................ 606/70, 71, 74, 282, 285, 324, 328
See application file for complete search history.

(56) References Cited

U.S. PATENT DOCUMENTS

| 3,926,193 A | 12/1975 | Hasson |
| 4,119,091 A | 10/1978 | Partridge |

(Continued)

FOREIGN PATENT DOCUMENTS

| DE | 10347173 B3 | 6/2005 |
| EP | 0201905 A2 | 11/1986 |

(Continued)

OTHER PUBLICATIONS

Spanish Search Report for ES2336059, dated Mar. 22, 2010, 2 pages, issued by The Spanish Office of Patent and Trademarks, Madrid, Spain (Partial Translation).

(Continued)

*Primary Examiner* — Andrew Yang
*Assistant Examiner* — Olivia C Chang
(74) *Attorney, Agent, or Firm* — Tim L. Kitchen; Peter B. Scull; Hamilton, DeSanctis & Cha, LLP

(57) ABSTRACT

A fixation device for the fixation of bone fragments, applicable to the mutual fastening of bone fragments temporarily separated during a surgical operation or as a result of a trauma. The device is also suitable for the fixation of a bone flap in the replacement thereof in a corresponding aperture made in the cranium or cranial bone mass. The device is made of biocompatible material and comprises a flexible strip and fastening means, the strip having a length allowing the formation of a fastening loop tightly fastening the bone fragments to be joined together. The fastening means are provided with at least one opening provided with interlocking means allowing the passage of a free end of the strip and preventing its extraction in the direction opposite to the insertion.

7 Claims, 6 Drawing Sheets

(56) References Cited

U.S. PATENT DOCUMENTS

| | | |
|---|---|---|
| 4,456,006 A | 6/1984 | Wevers et al. |
| 5,449,359 A | 9/1995 | Groiso |
| 5,743,913 A | 4/1998 | Wellisz |
| 5,788,698 A | 8/1998 | Savornin |
| 5,810,854 A | 9/1998 | Beach |
| 6,022,351 A | 2/2000 | Bremer et al. |
| 6,050,998 A | 4/2000 | Fletcher |
| 6,589,246 B1 | 7/2003 | Hack et al. |
| 6,921,401 B2 | 7/2005 | Lerch et al. |
| 6,969,391 B1 | 11/2005 | Gazzani |
| 7,238,188 B2 | 7/2007 | Nesper et al. |
| 8,403,930 B2 | 3/2013 | Chico Roca |
| 2004/0034375 A1 | 2/2004 | Ruiz et al. |
| 2004/0102779 A1 | 5/2004 | Nesper et al. |
| 2004/0116961 A1 | 6/2004 | Nesper et al. |
| 2005/0240189 A1 | 10/2005 | Rousseau et al. |
| 2006/0015106 A1 | 1/2006 | Lerch et al. |
| 2006/0259040 A1 | 11/2006 | Wellisz et al. |
| 2007/0270856 A1 | 11/2007 | Morales et al. |
| 2008/0172097 A1 | 7/2008 | Lerch et al. |

FOREIGN PATENT DOCUMENTS

| | | |
|---|---|---|
| EP | 1171050 B1 | 10/2004 |
| EP | 1477122 A2 | 11/2004 |
| FR | 2357229 A1 | 2/1978 |
| JP | 2001-25141 A | 1/2001 |
| JP | 2003-512885 A | 4/2003 |
| WO | WO0049949 A1 | 8/2000 |

OTHER PUBLICATIONS

International Search Report and Written Opinion of the International Searching Authority (Corrected Version), International Application No. PCT/EP2008/060279, Date of mailing Apr. 29, 2009, 16 pages, issued by the European Patent Office, Rijswijk Netherlands.

English Translation of the "Notice of Grounds for Rejection" issued by the Japanese Patent Office on JP Patent Application No. 2010-519454, Feb. 5, 2013, 2 pages, Tokyo Japan.

FIXATION DEVICE FOR THE FIXATION OF BONE FRAGMENTS

TECHNICAL FIELD OF THE INVENTION

The invention relates to a fixation device for the fixation of bone fragments, applicable to the mutual fastening of bone fragments temporarily separated during a surgical operation or as a result of trauma. The device according to the invention is also suitable for the fixation of a bone flap in the replacement thereof in a corresponding aperture made in the cranium or cranial bone mass.

BACKGROUND OF THE INVENTION

When under certain circumstances bone tissue is fractured or broken, it must be welded together again in order to recover its initial state. To that end there are many different devices which are used in the event of breaking due to trauma or accident, or in the event that bone tissue must be previously broken or fractured in the operating room in order to perform surgery.

The devices used to join bone fragments generally consist of clamps, the parallel ends of which are inserted into each of the bone fragments to be joined together. An example of this type of device is the one described in patent EP 1171050 B1, in which the two fragments of the sternum that must be joined together after a surgical operation on the chest (cardiovascular, pulmonary . . . ) are fixed by the action of a C-shaped clamp with a center piece from which ends opposite to one another originate, said clamp provided with a loop in the area of the center piece which is deformed when cooled to be able to apply the ends to the bone fragments of the sternum and which, once applied on the bone mass, returns to its original shape when it reaches body temperature, comprising the mentioned ends and therefore the joining of the fragments.

Other clamp-shaped devices are described, each having its own particularities, in patent documents U.S. Pat. No. 5,449,359, U.S. Pat. No. 5,788,698, U.S. Pat. No. 4,456,006 and U.S. Pat. No. 484,328.

Alternatively, surgical connectors can also be used to join bone fragments such as the connector described in U.S. Pat. No. 5,743,913 A1, in which a slightly curved plate provided with multiple openings and nodes homogenously distributed therethrough comprises at least three also slightly curved extensions or ribs joined to at least three of these nodes and suitable for receiving fastening means, such as screws.

All these devices involve the drawback that they are difficult to apply, requiring the use of applicator devices and/or additional instruments that are also very complex, or requiring additional elements for securing them in the bone fragments that must be joined together.

In the same manner, devices are widely used in the field of neurosurgical operations for the fixation of flaps or bone fragments which are generally provided with means for the fastening of the flaps, and suitable for being supported on or containing the cranial bone mass in a space reserved for such purpose, or by incision by means of a sharp element in said cranial mass. These devices are placed between the flap and the cranial bone, and except in the event that they are made of a biodegradable or absorbable material, they are permanently placed in the cranium.

One of the existing and widely used types of flap fixation devices generically consists of a device with two considerably circular elements facing one another in the form of semi-spherical caps joined by means of a shaft or shank through which the semi-spherical elements can be moved closer to one another in order to adjust the device to the cranium and flap bone mass thickness. Once the mentioned device is adjusted, both the flap and the cranial bone mass are supported between the semi-spherical elements, forming the bearing and supporting means of the flap and of the cranium. In this type of device, the neurosurgeon cuts the excess remaining shank once it is well placed between bone masses.

Patent document EP 1477122 A2 describes a device such as those described in the preceding paragraph consisting of an implant for adjacent cranial bone fragment fixation, comprising two fastening elements, an end element and an inner element, which by means of a joining element, which is wire, that is adjustable and can be led through the external fastening element, causes the sliding of the inner fastening element, which comes close to the external fastening element, said wire being led through multiple openings made in the fastening elements. The device described in EP1477122 A2 comprises additional joining means between the internal and external fastening elements, such as shafts perpendicular to the mentioned internal and external fastening elements, which can consist of ratchet teeth systems, clips or fragments with a trapezium- or triangular-shaped longitudinal section with side-projecting tips.

Patent document WO00/49949 likewise describes a fixation system comprising a fastening element of biocompatible material consisting of a disk-shaped head and a shank, in which said shank has a surface having ratchet teeth thereon, said fastening element consisting of a second, also disk-shaped, closure element, provided with an opening through which the shank can be inserted for the purpose of bringing the two disk-shaped elements together until the upper and lower edges of the bone fragments to be joined together.

These types of devices such as those described in patent document WO00/49949 are difficult to manufacture and store because of their size and because of the fact that they consist of an element from the central part of which there extends a shaft that is integral and perpendicular to the plane defined by the same, and they are subjected to a more demanding load state since the load is concentrated in the joint between the shaft and the disk-shaped head, whereby existing a higher probability of failure, especially when it is made with non-metallic materials.

Furthermore, many of these devices comprising two plates or elements joined by a rigid shaft involve the drawback that their entire surface does not adapt to different thicknesses and irregularities of the cranium and/or flap, resulting from the actual anatomy of this party of the body.

Most of these devices, specially designed to join bone flaps to the cranial bone mass, must be applied with the use of complex instruments, such as applicators suitable for engaging the shaft or shank joining the disk-shaped elements; and provided with means of pushing one of said disks, which is moved over the mentioned shaft in order to be close to its homologue.

The object of this invention provides novel solutions to the problems of manufacture, storage, resistance, adaptation to bone thicknesses and placement of bone fragment particularly bone flap, fixation devices. It is furthermore easy to apply due to simple elements provided in the actual fixation device and allows the possibility of being adjusted without the need for additional instruments.

DISCLOSURE OF THE INVENTION

The fixation device for the fixation of bone fragments object of the present invention is essentially characterized in that, being made of biocompatible material, it comprises a flexible strip and fastening means, the strip having a length allowing the formation of a fastening loop tightly fastening the bone fragments to be joined together, the fastening means being provided with at least one opening provided with interlocking means allowing the passage of a free end of the strip and preventing its extraction in the direction opposite to its insertion.

According to another feature of the invention, the strip has a length such that it allows the formation of a fastening loop tightened around of the bone fragments to be fastened, and the fastening means are arranged at one of the ends of the strip, being provided with an opening for the passage of the opposite end of the strip.

According to a variant of interest, for the object of maximally hugging the bone fragments encircled by the strip, the opening for the passage of the fastening means is oriented such that the portion of strip retained by the interlocking means is arranged such that it is essentially tangential to the formed loop.

In a particular embodiment, the fastening means are arranged in a closure plate, intended for being applied against the surface of the bone fragments and forming together with the strip one and the same body which is susceptible of adopting an essentially planar position in an inoperative position.

According to another variant of the invention, particularly intended for the fixation of a bone flap in the replacement thereof in a corresponding aperture made in the cranium or cranial bone mass, the device comprises two essentially planar plates connected by means of the flexible strip, one of which plates is a closure plate, intended for being applied against a face of the bone fragments, provided with the fastening means; and the other plate is a support plate, intended for being applied against another face of the mentioned bone fragments.

According to a preferred embodiment, the support plate is arranged integral and forming a single piece with the strip, or longitudinally movable, between the two ends of the mentioned strip, forming an assembly which is susceptible of adopting an essentially planar position in an inoperative position.

According to another feature of this variant of the invention, the closure plate is a detachable plate, the fastening means being provided with two openings for the passage of respective opposite ends of the strip.

In one embodiment the device incorporates auxiliary gripping means making it easier to handle the device and regulate the tightness of the closure plate against the outer face of the bone fragments.

According to another variant of the invention, also intended for the fixation of a bone flap in an aperture made in the cranium, the closure plate is integral with one of the ends of the strip, forming a single piece with the strip, the fastening means being provided with an opening for the passage of the opposite end of the strip.

With regard to the configuration of the strip, according to another feature of the invention, such strip is provided with a rough surface on at least one of its faces, a series of projections being formed which are suitable for collaborating with the interlocking means of the opening or openings, as the case may be, of the irreversible fastening means.

BRIEF DESCRIPTION OF THE DRAWINGS

The attached drawings show by way of a non-limiting illustration several embodiments for a fixation device for the fixation of bone fragments according to the invention. In said drawings:

FIGS. 3 to 7 are depictions of different variants, or views of one and the same variant, of devices suitable for the fixation of a bone flap in an aperture made in the cranium or cranial bone mass, of which:

FIG. 3 is a perspective view of a third variant of the device in an inoperative position, in which it has an essentially planar shape;

FIG. 4 is a perspective view of a fourth variant of the device also in an inoperative position, in which it has an essentially planar shape;

FIG. 5 is a view of the device according to FIG. 4 during a surgical intervention;

FIG. 7 is a view of the device according to FIG. 3 provided with auxiliary gripping means.

DETAILED DESCRIPTION OF THE DRAWINGS

Figure 1:
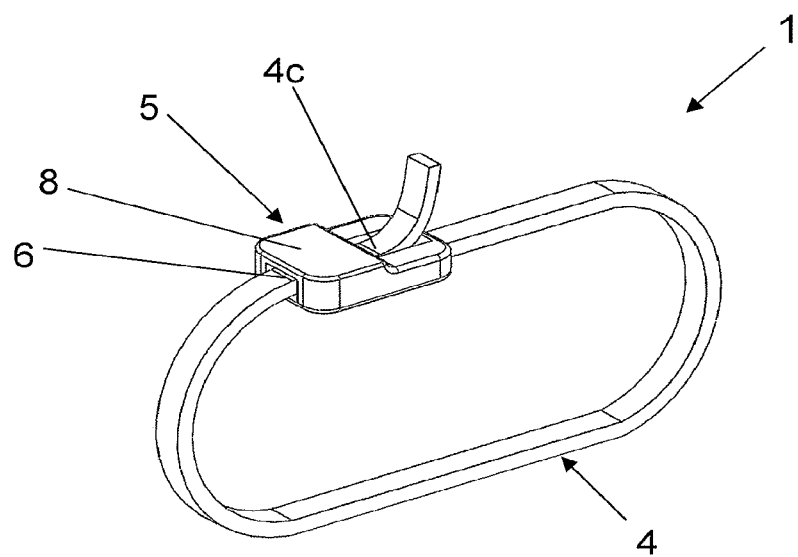
FIGS. 1 and 2 are perspective views of respective variants of the device according to the invention in which the strip forms a long enough loop so as to encircle the bone fragments to be fastened.
Figure 2:
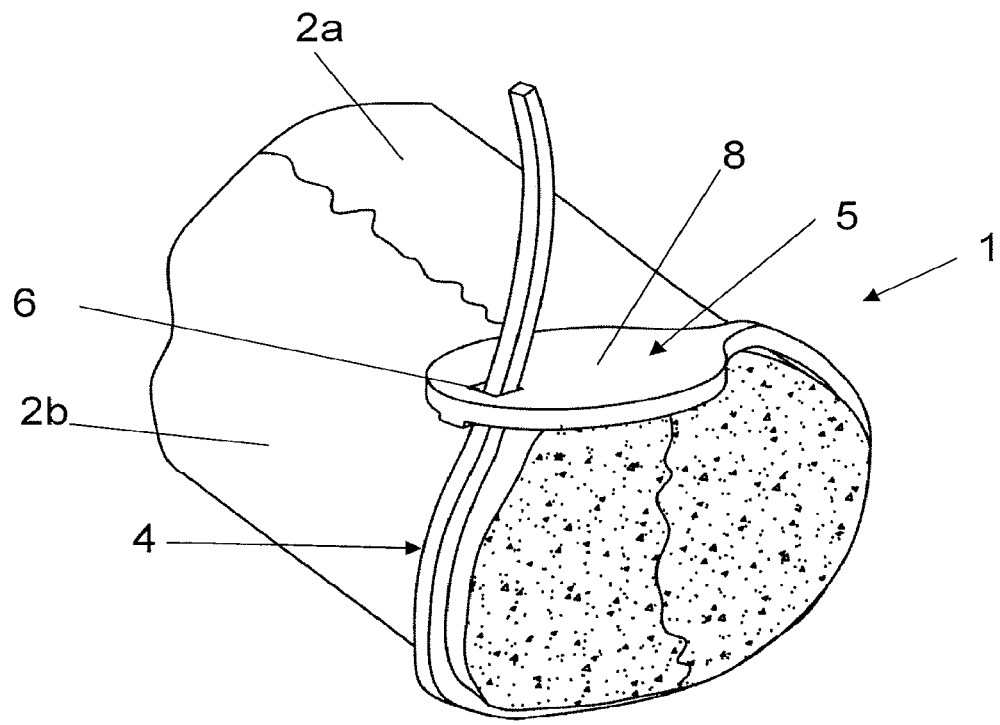

FIGS. 1 and 2 show first and second variants of the device 1 according to the invention for the joining of bone fragments, for example for the joining of two fragments 2a and 2b of a tibia (see FIG. 2).

The device 1 of FIG. 1 comprises a flexible strip 4, having a length allowing the formation of a fastening loop tightened around the bone fragments to be fastened, and irreversible fastening means 5 arranged at one of the ends of the strip 4. Said fastening means 5 are provided with an opening 6 which is provided with interlocking means 7 allowing the passage of the free end of the strip 4 and preventing its extraction in the direction opposite to its insertion.

In the variant of FIG. 1, the opening 6 for the passage of the fastening means 5 is oriented such that the portion of strip 4c retained by the interlocking means 7 is arranged such that it is essentially tangential to the formed loop, whereby the strip can completely hug the bone fragments, especially when the fractured bone has a circular section.

In the variant of FIG. 2, the fastening means 5 are arranged in an essentially planar closure plate 8 intended for being applied against the surface of the bone fragments 2a and 2b.

Figure 3:
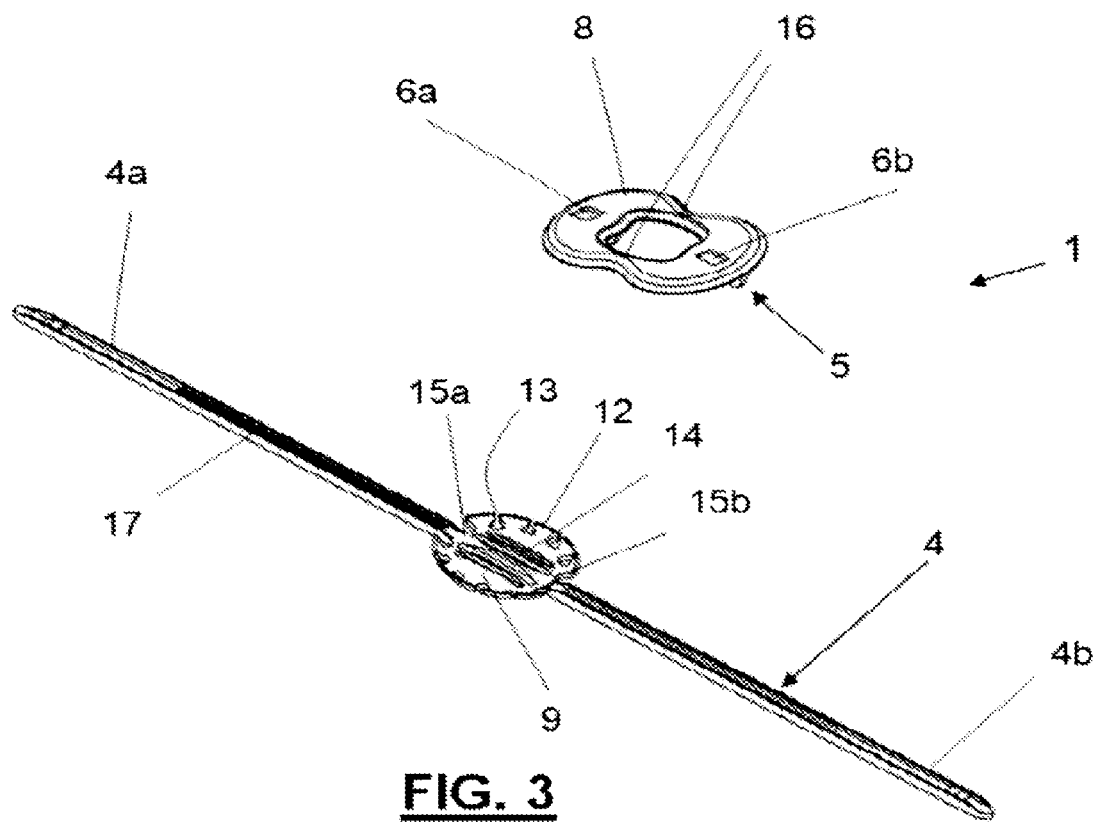
Figure 4:
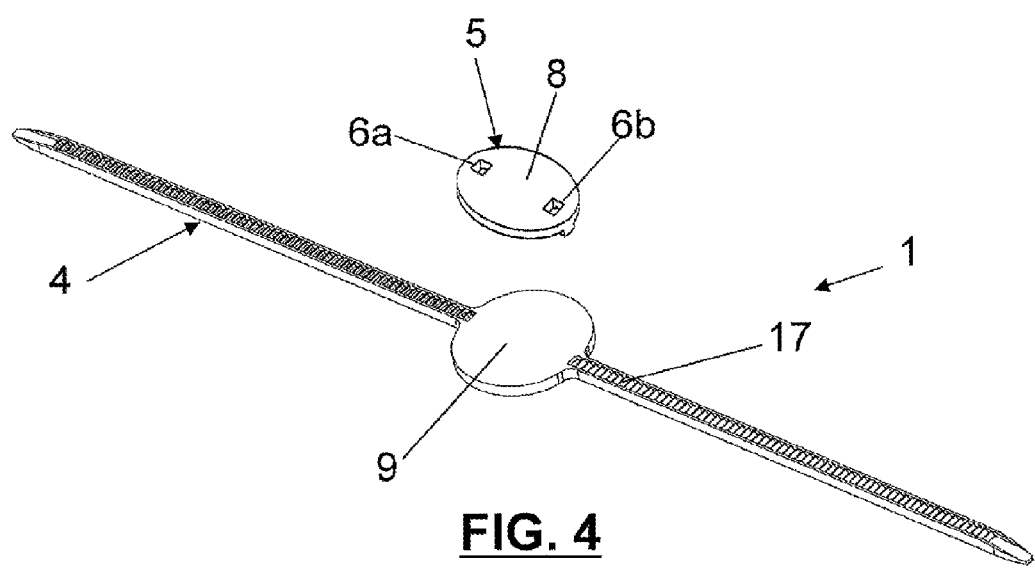

FIGS. 3 and 4 depict third and fourth variants of particular embodiments suitable for the fixation of a bone flap in an aperture made in the cranium or cranial bone mass. In both embodiments the device 1 comprises two plates connectable by means of the strip 4 flexible, one of which plates is a support plate 9, intended for being applied against the inner face of the mentioned bone fragments, and the other one is a closure plate 8, intended for being applied against the outer face of the mentioned bone fragments. The support plate 9 is a plate arranged between the two ends of the mentioned strip 4, respective opposing strip segments 4a and 4b being formed on both sides of the strip 4. The support plate 9 is integrally formed together with the body of the strip 4, forming a single body which adopts an essentially planar position when it is not operative.

With regard to the closure plate 8, it is detachable and provided with fastening means 5, which are provided with two openings 6a, 6b for the passage of respective opposite ends of the strip 4 for the formation of a closed loop as will be explained in detail below.

FIG. 3 shows that the support plate 9 is provided in its entire contour with multiple peripheral, flexible and elastic flanges 12, radially directed, in a somewhat inclined plane, from the plane of the support plate 9 towards the bone fragments on which said support plate 9 is intended to be supported. Advantageously, each flange 12 is separated from the adjacent flanges by respective cuts 13 made in the periphery of the support plate 9, such that the flanges 12 are wider at their outer end than at their joining to the support plate 9. The support plate 9 is likewise provided at its central portion with a plurality of ribs 14 arranged parallel to the plane in which the two strip segments 4a and 4b are inscribed.

It can also be seen in FIG. 3 that the strip segments 4a and 4b are joined diametrically opposite to the support plate 9 at respective areas of smaller section 15a, 15b than that of the rest of the support plate 9.

The areas of smaller section 15a and 15b along with the ribs 14 make it easier for the support plate 9 to adapt to the inner face of the cranial bone mass, allowing it to slightly bend, when the strip segments 4a and 4b exert pressure around the shaft marked by the direction of the ribs 14.

These features give the support plate 9 better gripping on the surface of the bone fragments and ensure that the strip 4, once the loop is formed and tightened, remains tensed due to the pulling effect that the flanges 12 transmit to the support plate 9 since the flanges want to recover their original position.

In the variant of FIG. 3, the closure plate 8 is provided with a partially weakened transverse area 16, suitable for giving the plate sufficient flexibility for the best possible coupling to the irregular configuration of the bone surface on which it must be supported. It thus achieves that the closure plate 8 can slightly bend along an imaginary line passing through the weakened areas of the closure plate 8, thus adapting to the outer face of the cranial bone mass, said shaft being advantageously perpendicular to the shaft which the support plate 9 bends, whereby achieving better support of the device 1 to the cranial bone mass.

Figure 5:
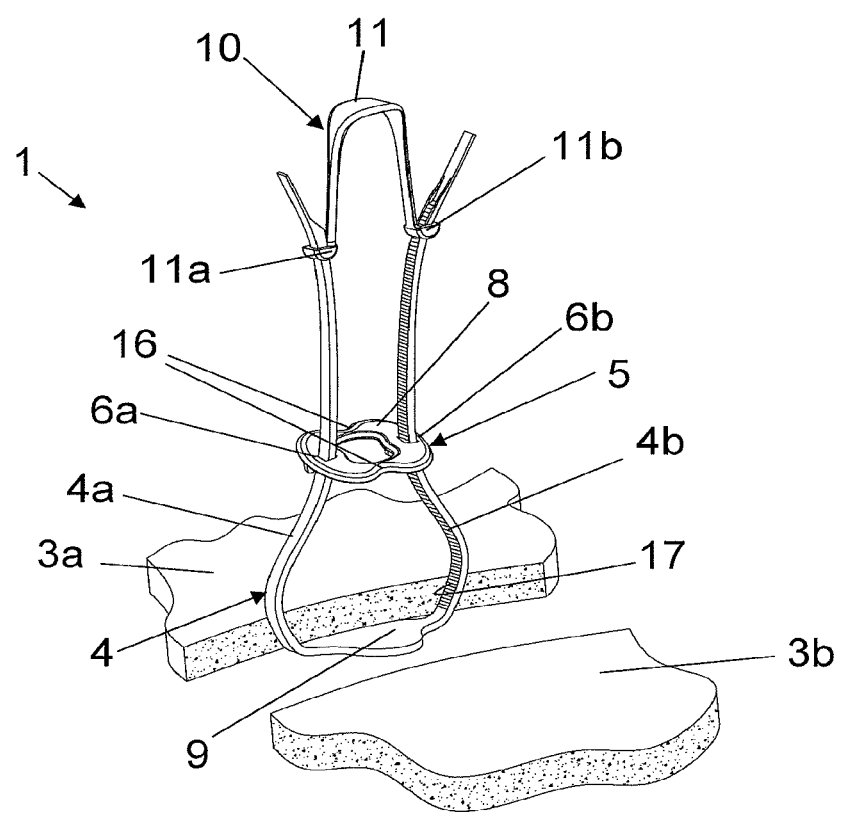

FIG. 5 depicts a device formed by the combination of a strip 4 according to the device according to FIG. 4 and a closure plate 8 according to the device of FIG. 4. In this FIG. 5 the free ends of the strip segments 4a and 4b have been inserted through the openings 6a and 6b, respectively, of the fastening means 5 provided for such purpose in the closure plate 8, a closed loop connecting the support plate 9 and the closure plate 8 having been formed.

Figure 6A:
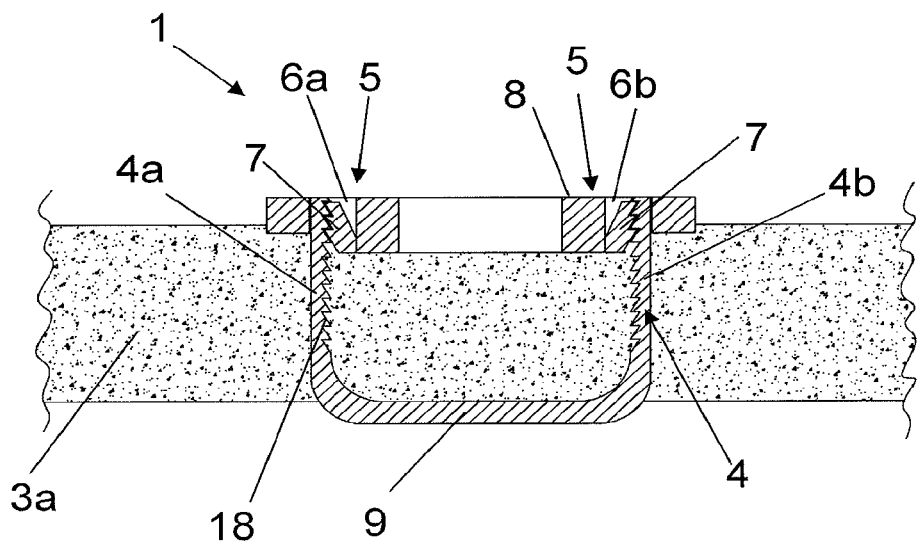
FIG. 6a is a section view of the device according to FIG. 4 in its operative position.
Figure 6B:
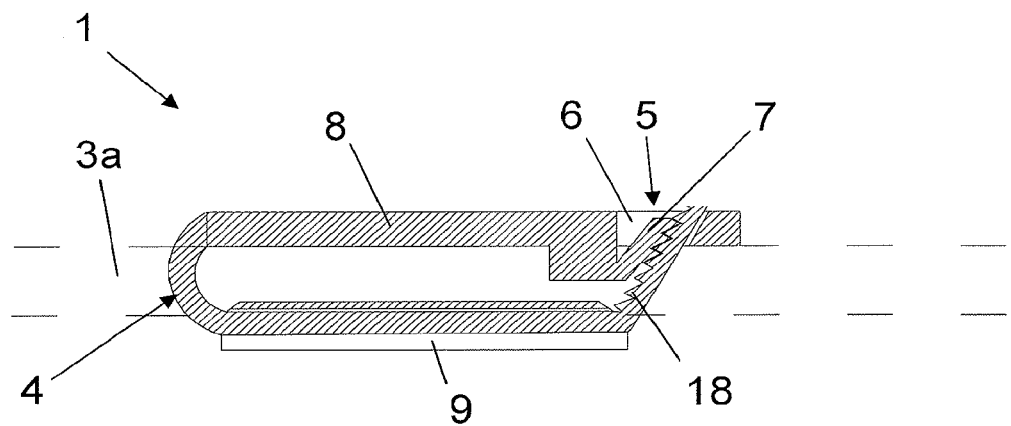
FIG. 6b is a view similar to that of FIG. 6a of a device according to a fifth variant of the invention.

During the application of the device 1, the support plate 9 is first supported against the inner face of the outer edges of the cranial bone mass 3a and of the bone flap 3b, and the closure plate 8 subsequently slides along the strip segments 4a and 4b towards the outer face of the cranial bone mass 3a and the flap 3b until being applied against said outer face. Then the strip segments 4a and 4b are cut to the level of the closure plate 8, depicted in FIG. 6a, the device 1 thus being placed in an operative position.

For the purpose of making it easier to slide the closure plate 8 towards the bone mass, the invention envisages incorporating auxiliary gripping means to thus simultaneously grip both strip segments 4a and 4b and keep them tensed with one hand, such that with the other hand the closure plate 8 can be slid along the two strip segments 4a and 4b also simultaneously.

Figure 7:
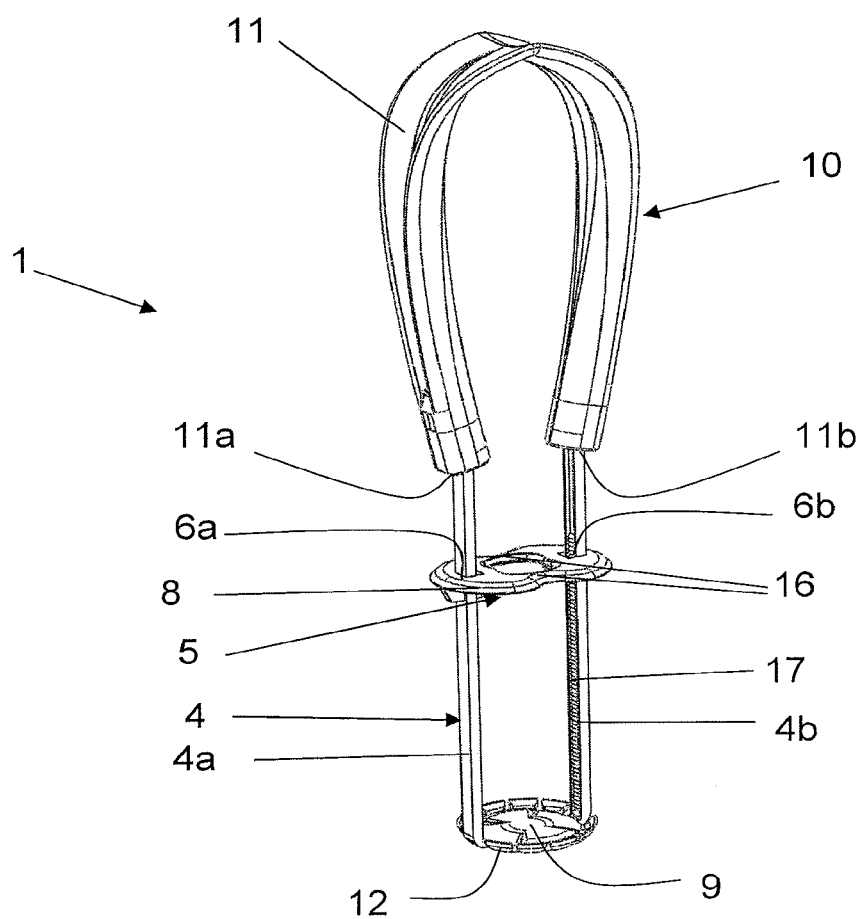

In the variants of FIGS. 5 and 7, the mentioned gripping means 10 are formed by a handle 11 the ends of which are provided with respective openings 11a and 11b provided with respective interlocking means allowing the passage of corresponding free ends of the segments 4a and 4b of the strip 4, preventing their extraction in the direction opposite to their insertion. These interlocking means can be formed similarly to the interlocking means, detailed below, provided in the openings 6a and 6b of the fastening means 5 of the closure plate 8.

Once the device 1 is positioned in the aperture of the cranium, the gripping means 10 prevent the support plate 9 from being moved and hitting against soft tissue (brain) and damaging it when the surgeon begins the movement of the closure plate 8 towards the support plate 9, without the need for additional instruments.

Alternatively, said gripping means 10 can consist of, with an equivalent function, respective extensions perpendicular to the free ends of the strip segments 4a and 4b, like knobs. The gripping means 10 can also consist of the joining of the ends of the strip segments 4a and 4b, for example by fusing the materials forming them, as shown in FIG. 8.

Figure 8:
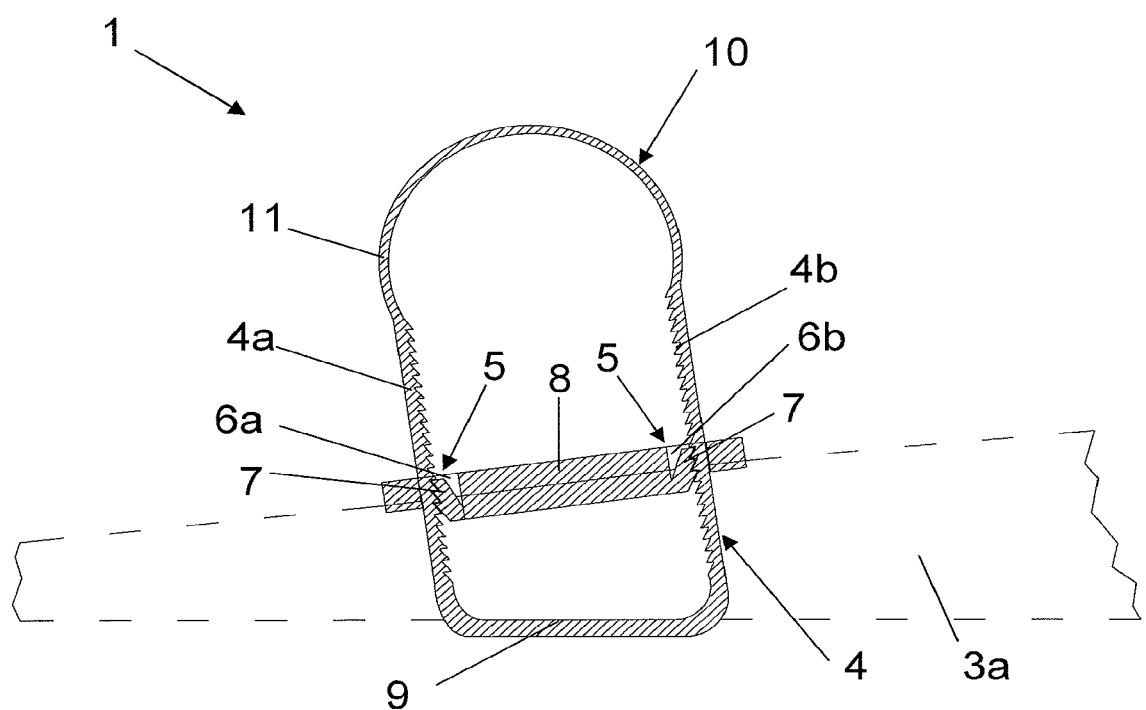
FIG. 8, is a view of a sixth variant of the invention, in an operative position, illustrating its adaptability to a cranium with irregular thickness.

FIG. 8 depicts another variant of the device according to the invention in which, unlike the devices of FIGS. 3 to 7, the closure plate 8 is integral with one of the ends of the strip 4, forming a single piece with it, and in which the fastening means 5 are provided with a single opening 6 for the passage of the opposite end of the strip 4. In this variant, for the purpose of being able to regulate the separation distance between the support plate 9 and the closure plate 8, adjusting it to the thickness of the cranial bone mass 3a, the support plate 9 is suitable for being longitudinally movable along the strip 4. For such purpose, the support plate 9 is preferably provided with a through opening longitudinally traversing the support plate 9, through which the strip 4 passes. According to another embodiment, the support plate 9 can be provided with a longitudinal groove in its outer face, having a width similar to the width of the strip 4, inside of which the mentioned strip 4 would be tightly housed when the loop is formed and the support plate 9 is applied, under pressure, against the inner face of the bone mass.

This variant of the invention can also apply in the case of wanting to join cracked or broken bone fragments, such as bones with considerably circular cross section (tibias, fibulas, ulnas, ribs, etc.). It can also apply in operations in which the sternum must be cut along the longitudinal axis, for example, when it is necessary to access the organs in the upper part of the chest, such as the heart or lungs.

The fastening means 5 of the device 1 are commonly arranged in the closure plate 8 in all the variants of the device 1 depicted in FIGS. 2 to 8. Even though in some variants the fastening means are provided with two openings for the passage of two free ends of the strip 4 and in other variants with a single opening, these openings have a contour that is complementary or similar to the cross section of the strip 4 and are provided with interlocking means 7 visible in the examples of FIGS. 6a, 6b and 8.

The mentioned interlocking means 7 consist of an elastic tab, formed integrally with the body of the closure plate 8, having a catch effect, cooperating with a ratchet tooth system provided at least at the apical ends or end of the strip 4. The ratchet tooth system comprises a rough surface 17 on at least one of the faces of the strip 4, there being formed a series of consecutive projections 18 suitable for collaborating with the interlocking means 7 of the opening or openings, as the case may be, through which the strip 4 is passed. The elastic tabs prevent and block the backward movement of the strip 4, ensuring the closure of the formed loop.

Preferably, the rough surface 17 is provided only on the inner face of the strip 4, because damage to adjacent structures is thus prevented.

The device 1 according to the invention is widely advantageous in its transport and use because first in its inoperative position of storage or distribution, it takes up little space and can be completely planar without later compromising its functionality. This inoperative position makes it easier to transport and distribute the devices 1, which can be stored or distributed in small size and small volume packages, such as envelopes or relatively thin cases.

In addition, the device 1 allows being applied to individuals with variations regarding the thickness of the bone since long enough strips 4 are envisaged for being adapted to different bone thicknesses. Furthermore, the same device 1 perfectly adapts, without the formation of projections, being uniformly tensed on its entire surface, to the different thicknesses that may existing in one and the same bone fragment of an individual.

This is particularly relevant because the reality of individuals indeed shows that one and the same person may present thickness variations in one and the same bone, not just because of anatomy but also because of particularities of each individual. It is thus known that the cranium presents areas of different thicknesses, but furthermore, these areas are also subject to variability between individuals. All this inter- and intra-individual variability is solved with the fixation device 1 object of the invention, as shown in FIG. 8.

With a device 1 according to any one of the variants depicted in FIGS. 1 to 8, operations can be performed in a wide range of people of different ages and sexes, or even in different animal species.

Furthermore, the devices 1 are easy to manufacture by common material molding or injection techniques.

Regarding the type of materials used for the manufacture of the fixation device 1 according to the invention, it is possible to use any material of those known as biocompatible polymeric material, biocompatible metal allows, ceramics or composites of the foregoing. Generally, biocompatible, implantable and/or osteo-integratable materials are chosen, i.e., materials producing minimum reaction when introduced in the animal or human body and which can furthermore make the neoformation or regeneration of bone tissue easier, the device be osteo-integrated and/or finally reabsorbed by the body after sufficient time has passed for the groove, opening or cut to have been filled in with new tissue. These materials can furthermore be radiotransparent.

The invention claimed is:

1. A method of fixating a cranial bone flap with a cranial bone mass that involves the use of a fixation device that has a support plate with an inner surface that is adapted to be applied against the inner face of the outer edges of the cranial bone mass and the cranial bone flap, the support plate having first and second peripheral edges, a first flexible strip segment extending from the first peripheral edge and a second flexible strip segment extending from the second peripheral edge, the first and second flexible strip segments being integral and forming a single piece with the support plate, the fixation device having a closure plate with an outer surface and an inner surface, the inner surface adapted to be applied against the outer face of the outer edges of the cranial bone mass and the cranial bone flap, the closure plate having first and second openings extending there through, each of the first and second openings adapted to respectively receive the first and second flexible strip segments, each of the first and second openings having associated therewith an interlocking feature that permits the passage and movement of the first and second flexible strip segments in a first direction through the respective first and second openings while preventing movement in a second direction opposite the first direction, the first and second flexible strip segments extend through the respective first and second openings of the closure plate to form with the support plate a closed loop, the closure plate being moveable along the first and second flexible strips in a direction toward the support plate, the fixation device having a handle with a first end and a second end, a portion of the first and second flexible strip segments respectively coupled to the first and second ends, the closure plate being positioned on the first and second flexible strip segments between the handle and the support plate, the method comprising:

placing the inner surface of the support plate against the inner face of the outer edges of the cranial bone mass and the cranial bone flap, with the use of a first hand applying tension to the first and second flexible strip segments by gripping and pulling the handle in the first direction to prevent the support plate from being moved and hitting against soft brain tissue without the need for additional instruments, with the use of a second hand sliding the closure plate along the first and second flexible strip segments toward the outer face of the cranial bone mass and cranial bone flap until the inner surface of the closure plate is applied against the outer face; and severing each of the first and second flexible strip segments at the outer surface of the closure plate.

2. The method according to claim 1, wherein the support plate is at least partially conformable to the inner face of the outer edges of the cranial bone mass and the cranial bone flap and the closure plate is at least partially conformable to the outer face of the outer edges of the cranial bone mass and the cranial bone flap, the method comprising applying with the second hand during the step of sliding sufficient pressure to the closure plate to cause the closure plate to at least partially conform to the outer face of the outer edges of the cranial bone mass and the cranial bone flap.

3. The method according to claim 2, wherein while using the second hand to slide the closure plate along the first and second flexible strip segments toward the outer face of the cranial bone mass and cranial bone flap until the inner surface of the closure plate is applied against the outer face, also applying tension to the first and second flexible strip segments by gripping and pulling the handle in the first direction by the first hand to cause the support plate to at least partially conform to the inner face of the outer edges of the cranial bone mass and the cranial bone flap.

4. A method of fixating a cranial bone flap with a cranial bone mass that involves the use of a fixation device that has a substantially planar support plate with an inner surface that is adapted to be applied against the inner face of the outer edges of the cranial bone mass and the cranial bone flap, the support plate having first and second geometrically opposed peripheral edges, a first flexible strip segment extending from the first peripheral edge and a second flexible strip segment extending from the second peripheral edge, the first and second flexible strip segments being integral and forming a single piece with the support plate, the fixation device having a substantially planar closure plate with an outer surface and an inner surface, the inner surface adapted to be applied against the outer face of the outer edges of the cranial bone mass and the cranial bone flap, the closure plate having first and second openings extending there through, each of the first and second openings adapted to respectively receive the first and second flexible strip segments, each of the first and second openings having associated therewith an interlocking feature that permits the passage and movement of the first and second flexible strip segments in a first direction through the respective first and second openings while preventing movement in a second direction opposite the first direction, the first and second flexible strip segments extend through the respective first and second openings of the closure plate to form with the support plate a closed loop, the closure plate being moveable along the first and second flexible strips in a direction toward the support plate, the fixation device having a handle with a first end and a second end, a portion of the first and second flexible strip segments respectively secured to the first and second ends, the closure plate being positioned on the first and second flexible strip segments between the handle and the support plate, the method comprising:

placing the inner surface of the support plate against the inner face of the outer edges of the cranial bone mass and the cranial bone flap, with the use of a first hand applying tension to the first and second flexible strip segments by gripping and pulling the handle in the first direction to prevent the support plate from being moved and hitting against soft brain tissue without the need for additional instruments, with the use of a second hand sliding the closure plate along the first and second flexible strip segments toward the outer face of the cranial bone mass and cranial bone flap until the inner surface of the closure plate is applied against the outer face; and severing each of the first and second flexible strip segments at the outer surface of the closure plate.

5. The method according to claim 4, wherein the support plate is at least partially conformable to the inner face of the outer edges of the cranial bone mass and the cranial bone flap and the closure plate is at least partially conformable to the outer face of the outer edges of the cranial bone mass and the cranial bone flap, the method comprising applying with the second hand during the step of sliding sufficient pressure to the closure plate to cause the closure plate to at least partially conform to the outer face of the outer edges of the cranial bone mass and the cranial bone flap.

6. The method according to claim 5, wherein while using the second hand to slide the closure plate along the first and second flexible strip segments toward the outer face of the cranial bone mass and cranial bone flap until the inner surface of the closure plate is applied against the outer face also applying tension to the first and second flexible strip segments by gripping and pulling the handle in the first direction by the first hand to cause the support plate to at least partially conform to the inner face of the outer edges of the cranial bone mass and the cranial bone flap.

7. A method of fixating a cranial bone flap with a cranial bone mass that involves the use of a fixation device that has a support plate with an inner surface that is adapted to be applied against the inner face of the outer edges of the cranial bone mass and the cranial bone flap, the support plate at least partially conformable to the inner face of the outer edges of the cranial bone mass and the cranial bone flap and having first and second peripheral edges, a first flexible strip segment extending from the first peripheral edge and a second flexible strip segment extending from the second peripheral edge, the first and second flexible strip segments being integral and forming a single piece with the support plate, the fixation device having a flexible closure plate with an outer surface and an inner surface, the inner surface adapted to be applied against the outer face of the outer edges of the cranial bone mass and the cranial bone flap, the closure plate at least partially conformable to the outer face of the outer edges of the cranial bone mass and the cranial bone flap and having first and second openings extending there through, each of the first and second openings adapted to respectively receive the first and second flexible strip segments, each of the first and second openings having associated therewith an interlocking feature that permits the passage and movement of the first and second flexible strip segments in a first direction through the respective first and second openings while preventing movement in a second direction opposite the first direction, the first and second flexible strip segments extend through the respective first and second openings of the closure plate to form with the support plate a closed loop, the closure plate being moveable along the first and second flexible strips in a direction toward the support plate, the fixation device having a handle with a first end and a second end, a portion of the first and second flexible strip segments respectively secured to the first and second ends, the closure plate being positioned on the first and second flexible strip segments between the handle and the support plate, the method comprising:

placing the inner surface of the support plate against the inner face of the outer edges of the cranial bone mass and the cranial bone flap, with the use of a first hand applying tension to the first and second flexible strip segments by gripping and pulling the handle in the first direction to prevent the support plate from being moved and hitting against soft brain tissue without the need for additional instruments, with the use of a second hand sliding the closure plate along the first and second flexible strip segments toward the outer face of the cranial bone mass and cranial bone flap until the inner surface of the closure plate is applied against the outer face, applying with the second hand sufficient pressure to the closure plate to cause the closure plate to at least partially conform to the outer face of the outer edges of the cranial bone mass and the cranial bone flap while applying tension to the first and second flexible strip segments by gripping and pulling the handle in the first direction by the first hand to cause the support plate to at least partially conform to the inner face of the outer edges of the cranial bone mass and the cranial bone flap; and severing each of the first and second flexible strip segments along the outer surface of the closure plate.

\* \* \* \* \*